(12) United States Patent
Umer et al.

(10) Patent No.: US 10,126,108 B2
(45) Date of Patent: Nov. 13, 2018

(54) APPARATUS AND METHOD FOR CLASSIFYING ORIENTATION OF A BODY OF A MAMMAL

(75) Inventors: Muhammad Umer, Springvale (AU); Andrew James Ronchi, East Malvern (AU); Daniel Matthew Ronchi, Mornington (AU)

(73) Assignee: DORSAVI LTD, Melbourne East, Victoria (AU)

( * ) Notice: Subject to any disclaimer, the term of this patent is extended or adjusted under 35 U.S.C. 154(b) by 679 days.

(21) Appl. No.: 13/984,699

(22) PCT Filed: Feb. 9, 2012

(86) PCT No.: PCT/AU2012/000126
§ 371 (c)(1),
(2), (4) Date: Oct. 10, 2013

(87) PCT Pub. No.: WO2012/106770
PCT Pub. Date: Aug. 16, 2012

(65) Prior Publication Data
US 2014/0032124 A1 Jan. 30, 2014

(30) Foreign Application Priority Data
Feb. 10, 2011 (AU) ................. 2011900438

(51) Int. Cl.
*G01B 5/004* (2006.01)
*A61B 5/11* (2006.01)
(Continued)

(52) U.S. Cl.
CPC ............ *G01B 5/004* (2013.01); *A61B 5/1116* (2013.01); *A61B 5/1121* (2013.01); *G01B 5/24* (2013.01);
(Continued)

(58) Field of Classification Search
CPC ....... A61B 5/22; A61B 5/1116; A61B 5/1121; A61B 5/6823; A61B 2562/0219;
(Continued)

(56) References Cited

U.S. PATENT DOCUMENTS

| | | |
|---|---|---|
| 5,031,618 A | 7/1991 | Mullett |
| 2002/0170193 A1 | 11/2002 | Townsend et al. |
| 2009/0030345 A1 | 1/2009 | Bonnet et al. |

FOREIGN PATENT DOCUMENTS

| | | |
|---|---|---|
| CN | 1988847 A | 6/2007 |
| CN | 101366680 A | 2/2009 |

(Continued)

OTHER PUBLICATIONS

Lai, et al., "Adaptive Body Posture Analysis Using Collaborative Multi-Sensors for Elderly Falling Detection", IEEE Intelligent Systems, 2005, vol. 25(2), pp. 20-30.*

(Continued)

*Primary Examiner* — Linh Giang Le
(74) *Attorney, Agent, or Firm* — Mintz Levin Cohn Ferris Glovsky and Popeo, P.C.

(57) ABSTRACT

Apparatus is disclosed for providing classification of body orientation of a mammal. The apparatus includes means (10, 11) for measuring position of said body relative to a frame of reference at one or more points on the body, wherein said means for measuring includes at least one position sensor. The apparatus includes means (12) for providing first data indicative of said position; means (15) for storing said data at least temporarily; and means (13, 14) for processing said data to provide said classification of body orientation. A method for providing classification of body orientation of a mammal is also disclosed.

18 Claims, 5 Drawing Sheets

(51) Int. Cl.
*G01B 5/24* (2006.01)
*G01B 7/004* (2006.01)
*G01B 7/30* (2006.01)
*A61B 5/00* (2006.01)

(52) U.S. Cl.
CPC .............. *G01B 7/004* (2013.01); *G01B 7/30* (2013.01); *A61B 5/6823* (2013.01); *A61B 2562/0219* (2013.01)

(58) Field of Classification Search
CPC ........ G06Q 50/22; G06Q 50/24; G01B 5/004; G01B 7/30; G01B 5/24; G01B 7/004
See application file for complete search history.

(56) References Cited

FOREIGN PATENT DOCUMENTS

| | | |
|---|---|---|
| CN | 101394788 A | 3/2009 |
| CN | 101808593 A | 8/2010 |
| CN | 102149323 A | 8/2011 |
| JP | H11332852 A | 12/1999 |
| JP | 2002328134 A | 11/2002 |
| JP | 2005021450 A | 1/2005 |
| JP | 2007-241867 A | 9/2007 |
| JP | 2007244495 A | 9/2007 |
| JP | 2009039466 A | 2/2009 |
| JP | 2009-106377 A | 5/2009 |
| JP | 2009106390 A | 5/2009 |
| JP | 2010125239 A | 6/2010 |
| WO | WO-2005/115228 A1 | 12/2005 |

OTHER PUBLICATIONS

PCT Search Report dated Apr. 20, 2012 for PCT application No. PCT/AU2012/000126.

Extended European Search Report and Written Opinion issued in European Patent Application No. 12745356.1, dated Sep. 25, 2017. 6 pages.

First Examination Report dated Dec. 12, 2007 issued in Canadian Patent Application No. 2,827,113. 5 pages.

\* cited by examiner

APPARATUS AND METHOD FOR CLASSIFYING ORIENTATION OF A BODY OF A MAMMAL

CROSS REFERENCE TO RELATED APPLICATIONS

This application is a U.S. national phase application claiming the priority benefit under 35 U.S.C. § 371 to Patent Cooperation Treaty Application no. PCT/AU2012/000126, which was filed on Feb. 9, 2012 and which claims priority to Australian Patent Application No. 2011900438, which was filed on Feb. 10, 2011. The present invention is related to the method and apparatus described in International Patent Application PCT/AU2005/000743. The disclosure of each document referenced in this paragraph is incorporated herein by reference in its entirety.

FIELD OF THE INVENTION

The present invention relates to apparatus and a method for ascertaining and classifying orientation of the body of a vertebral mammal. The present invention is particularly suitable for classifying posture of a human subject at a given point in time and it will be described herein in this context. Nevertheless, it is to be understood that the present invention is not thereby limited to such applications. Classifying posture of a human subject includes ascertaining whether the subject is sitting, standing or lying down. Body orientation may encompass further levels of detail, including sitting upright, sitting slouched, kneeling, etc. as well as dynamic body orientations including walking, running, etc.

In this document use of the words orientation, standing, sitting and lying in relation to the body of a mammal includes a reference to an alignment or state, an erect, upright or seated posture and/or a horizontally positioned, reclined or slouched orientation of the body of the mammal.

BACKGROUND OF THE INVENTION

In many applications that relate to assessment of movement of the body of a human or other mammal, rehabilitation, strain or load monitoring, sports assessment, as well as design and construction of workplaces, an ability to make assessments about an activity may be improved by knowing a general orientation of the body of the human or mammal. This is because the forces acting on the trunk or any limb of the body may in general be significantly affected by the orientation of the body.

A number of physiological and biomechanical changes occur when for example a body moves from one orientation to another, e.g., sitting to standing or vice versa. In a biomechanical context, this movement may lead to changes in angular displacement of various anatomical landmarks with respect to one or more reference planes. Identification of body orientation may therefore require measurement of angular displacement with respect to a frame of reference. Angular displacement may be measured using position sensors such as accelerometers which provide a position referenced to gravity, magnetometers which provide a position referenced to earth's magnetic field, gyroscopes and/or optical sensors. The present invention may use a position sensor to detect angular displacement of one or more points on the body of a mammal such as one or more points on the spine and may use the displacements to identify various orientations of the body.

DESCRIPTION OF THE RELATED ART

Numerous techniques based on body mounted sensors have been reported in literature for automatic identification of body orientation or current activity being performed by a human. Typically, these techniques compute a likelihood of a posture by matching a sensor output to a set of prior signature outputs corresponding to a desired set of postures.

However, the prior art suffers from a number of disadvantages including:

(a) prior art techniques are not capable of deriving body orientation by position sensors placed on a spine;
(b) prior art techniques may be computationally intensive and require PC based offline processing;
(c) accuracy of some prior art techniques in differentiating between different static positions such as standing and sitting positions is relatively poor;
(d) some prior art techniques rely on transition detection, e.g. sitting to standing or vice versa which presents a drawback for real-time classification in which systems detect a current posture continuously. Missing a transition may result in a long duration of erroneous classification state;
(e) prior art techniques require calibration of the system for every subject so that signature values for various body orientations may be adjusted;
(f) some prior art systems are mercury based. Shortcomings of mercury based systems include the hazardous nature of mercury itself, the splashing of mercury inside a sensor during dynamic movements leading to false readings and an arduous calibration process.

The present invention may alleviate the disadvantages of the prior art or at the very least may provide the consumer with a choice.

SUMMARY OF THE INVENTION

According to one aspect of the present invention there is provided apparatus for providing classification of body orientation of a mammal, said apparatus including:
means for measuring position of said body relative to a frame of reference at one or more points on the body, wherein said means for measuring includes at least one position sensor;
means for providing first data indicative of said position;
means for storing said data at least temporarily; and
means for processing said data to provide said classification of body orientation.

According to a further aspect of the present invention there is provided apparatus for providing classification of body orientation of a mammal, said apparatus including:
a position sensor arranged for measuring position of said body relative to a frame of reference at one or more points on the body and for providing first data indicative of said position;
a non-transitory memory device coupled to the position sensor and arranged for storing said data; and
a processor coupled to the position sensor and arranged for processing said data to provide said classification of body orientation.

According to a further aspect of the present invention there is provided a method for providing classification of body orientation of a mammal, said method including:
measuring position of said body relative to a frame of reference at one or more points on the body, wherein said measuring is performed by means of at least one position sensor;

providing first data indicative of said position;
storing said data at least temporarily; and
processing said data to provide said classification of body orientation.

According to a further aspect of the present invention there is provided a method for providing classification of body orientation of a mammal, said method including:
using at least one position sensor to measure position of said body relative to a frame of reference at one or more points on the body and to provide first data indicative of said position;
storing said data in a non-transitory memory device; and
processing said data by a processor to provide said classification of body orientation.

The or each point on the body may be located on a spine of a vertebral mammal. The processing may be performed in real time to enhance accuracy and/or usefulness of the classification.

The means for processing may include a digital processor adapted to execute an algorithm for evaluating body orientation. The algorithm may include a dynamic classifier and a static classifier. The algorithm may include a transition classifier to enhance accuracy of the classification. The algorithm may include an adaptive module. The algorithm may evaluate body orientation based on assigning class signatures to primary body orientations including standing, sitting, lying down and dynamic (in motion). The algorithm may include a logic tree to identify posture based on recognition of a signature or pattern relating to each posture. A signature or pattern relating to each posture may be determined by a set of rules acquired during a training or learning phase. The algorithm may include unsupervised learning to modify a previously learned signature or pattern relating to a posture for an individual subject based on current data sensed for the individual subject.

The or each position sensor may be applied to the lumbar spine of the mammal. The or each position sensor may include at least one of an accelerometer, a gyroscope and a magnetometer. The position sensor may be adapted to measure angular displacement along three orthogonal axes.

The data may be used to derive displacement in an extension flexion plane. Additionally or alternatively the data may be used to derive displacement in a lateral flexion plane. The data may be used to derive rotation of the body. Each measuring means may include at least one A to D converter for converting analog data to a digital domain. The A to D conversion may take place prior to storing the data.

The means for measuring position may measure displacement in a lateral or side to side flexion plane. The means for measuring position may also measure displacement in an extension or front to back flexion plane. The means for measuring position may include means for measuring rotation. A measure of rotation may be derived from one or more accelerometers, one or more magnetometers, muscle activity and/or one or more gyroscopes.

The or each position sensor may include at least one accelerometer. The or each accelerometer may measure linear acceleration of the body or body part with which it is associated. The or each accelerometer may include structure for measuring acceleration simultaneously along one, two or three orthogonal axes. Displacement data may be derived for the or each accelerometer by a process of integration as is well known in the art. Alternatively or additionally data may be derived from one or more accelerometers to provide angular displacement or position relative to a reference such as a direction defined by gravity. The apparatus may include structure for deriving angular position from the acceleration data such as by calculating a forward tilt angle and a side tilt angle. The apparatus may include structure such as a gyroscope for deriving rotational position of the body part. Alternatively or additionally data may be derived from one or more magnetometers to provide angular displacement or position relative to a reference such as a direction defined by earth's magnetic field.

Transformation of Accelerometer Data to Position

According to one embodiment of the present invention, position data may be acquired by means of at least one accelerometer sensor. Each accelerometer may detect acceleration of a small mass mounted within a microchip on a PCB board. As the PCB board and the accelerometer move from one position to another, the mass may experience an acceleration at the start of the movement as well as a deceleration as the movement ceases. The accelerometer may convert movement of the mass into a voltage signal (typically in mV) that represents data in its most raw form.

For a resultant G force in three dimensions, three axes trigonometry may be used, wherein x is the horizontal axis, y is the vertical axis and z is the 'through page' axis. Using 3D Pythagoras and an inverse tangent formula, two angles may be derived to give a position for the accelerometer. One accelerometer in isolation may give only a direction of movement, but when there are two accelerometers, the difference between angles of the two accelerometers may represent a change in position (in degrees) of one accelerometer relative to the other accelerometer. This may allow the apparatus to calculate angular position of the spine, at any moment in time, within a three dimensional axis.

The following expressions may be used to derive angular changes from accelerometers.

$ep+o=1g\ fp+o=-1g$ where:

$e$=millivolts for 1 g $f$=millivolts for—1 g $p$=gain (multiplier) $o$=offset solving p and o:

$ep+o-fp-o=2\ g(e-f)p=2\ g$ $P\sim e-f\ ep+o=1g\ o-\backslash g-ep$ or $fp+o=-1g\ o=\sim\backslash g-Jp$ Note: values for p and o should be calculated for each axis.

$Xg\ ymVpy+Oy=Vg\ ZmVpz+Oz=Zg$

The above 3 equations show for the 3 axes the span and offset adjustment which converts millivolts to g.

The magnitude and tilt (forward/side) for the resultant vectors may be calculated as follows.

Magnitude: $r_g = \sqrt{x_g^2 + y_g^2 + z_g^2}$

The magnitude represents the vector sum in three dimensions of the resultant G force.

$$\text{Forward Tilt } \theta = \tan^{-1}\left(\frac{z_g}{\sqrt{x_g^2 + y_g^2}}\right)$$

The forward and side tilt angles. θ, β give the rotational position of the accelerometer relative to the Z and X axes respectively.

$$\text{Side Tilt } \beta = \tan^{-1}\left(\frac{x_g}{\sqrt{z_g^2 + y_g^2}}\right)$$

Transformation of Magnetometer Data to Position

According to another embodiment of the present invention, position data may be acquired by means of at least one magnetometer sensor. Each magnetometer may measure strength and/or direction of earth's magnetic field by a change or changes in resistance of a thin film deposited on a silicon wafer (anisotropic magnetoresistive magnetometers) or by a change or changes in a coil on a ferromagnetic core (magnetoinductive magnetomers). The coil may include a single winding and may form an inductance element in a L/R relaxation oscillator. A magnetometer may measure strength and/or direction of earth's magnetic field in one, two or three planes. Earth's North may be used as a reference to compute orientation of a body with assistance of three axis trigonometry.

The memory may receive data from the or each sensor. Each sensor may include or be associated with an analog to digital (A to D) converter. Alternatively, the or each sensor means may output analog data. The memory may include or be associated with one or more A to D converters to convert the analog data to a digital domain prior to storing the data. The apparatus may include a digital processor for processing the data. The processor may process the data in real time to provide bio-feedback to the person being monitored. The digital processor may include an algorithm for classifying body orientation. The digital processor may perform calculations with the algorithm.

The memory or data storing means may store data in digital format for later analysis and/or reporting. In one form the memory or data storing means may include memory structure for storing the digital data such as a memory card, memory stick, SSD or the like. The memory means may be removable to facilitate downloading the data to a remote processing device such as a PC or other digital processing engine.

The system of the present invention may include a user interface means. The user interface means may include a display screen and one or more controls such as buttons or the like to allow the user to interact with the data storing means.

A Body Orientation Classification (BOC) algorithm may be used to classify body orientation based on a combination of G forces, local earth field components and angular displacement data discerned from outputs of the one or more position sensors placed on the body. The BOC algorithm may be based on machine learning. The BOC algorithm may include a data driven approach to map a domain (a set of decision variables) to a range (a set of classes). In absence of a rigorous mathematical model to map each domain value to a range value, the BOC algorithm may identify patterns in the data and may perform a required mapping probabilistically based on the identified patterns.

The BOC algorithm may be based on the notion that each body orientation includes static and dynamic components and exhibits a signature or pattern in a form of a specific range or ranges of G-forces, local earth field components and angular displacements experienced by the body. The BOC algorithm may learn such signatures or patterns from data generated by a large population. The BOC algorithm may map position sensor outputs to the learnt patterns in real time and may discern a current body orientation therefrom. To modify a previously learned signature or pattern relating to a posture for an individual subject, the BOC algorithm may perform unsupervised classification of currently sensed data for the individual subject. A resulting class signature from this process may form a feedback loop to continuously improve a previous class signature.

DESCRIPTION OF THE DRAWINGS

A preferred embodiment of the present invention will now be described with reference to the accompanying drawings wherein.

DESCRIPTION OF A PREFERRED EMBODIMENT

Figure 1:
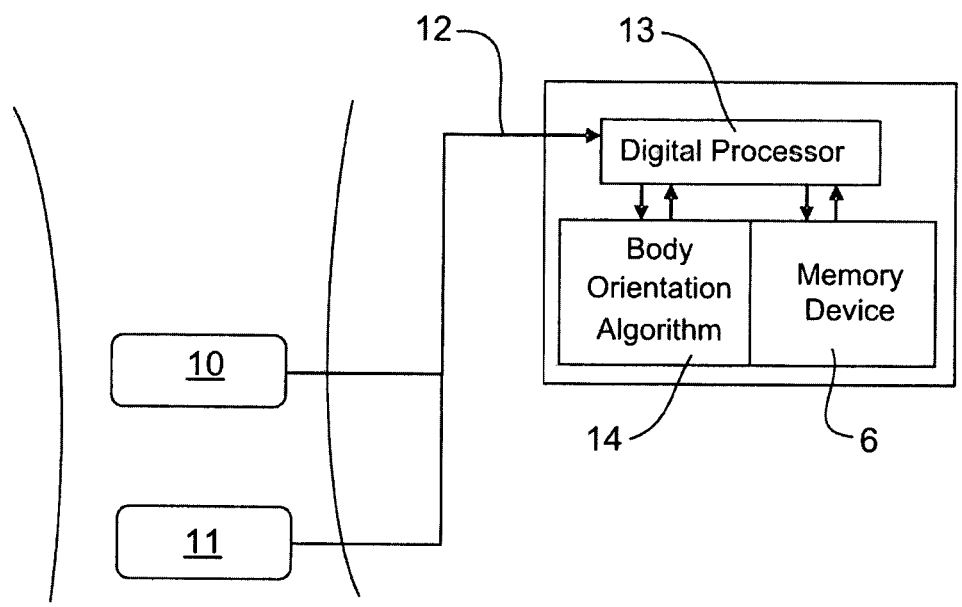
FIG. 1 shows one form of apparatus for classifying orientation of a body of a mammal.

FIG. 1 shows position sensors 10, 11 placed on a human spine. Position sensors 10, 11 are connected via wireless link 12 to a digital processor 13 adapted to execute a body orientation algorithm 14. A memory device 15 is associated with the digital processor 13 for storing data in digital format.

Figure 2:
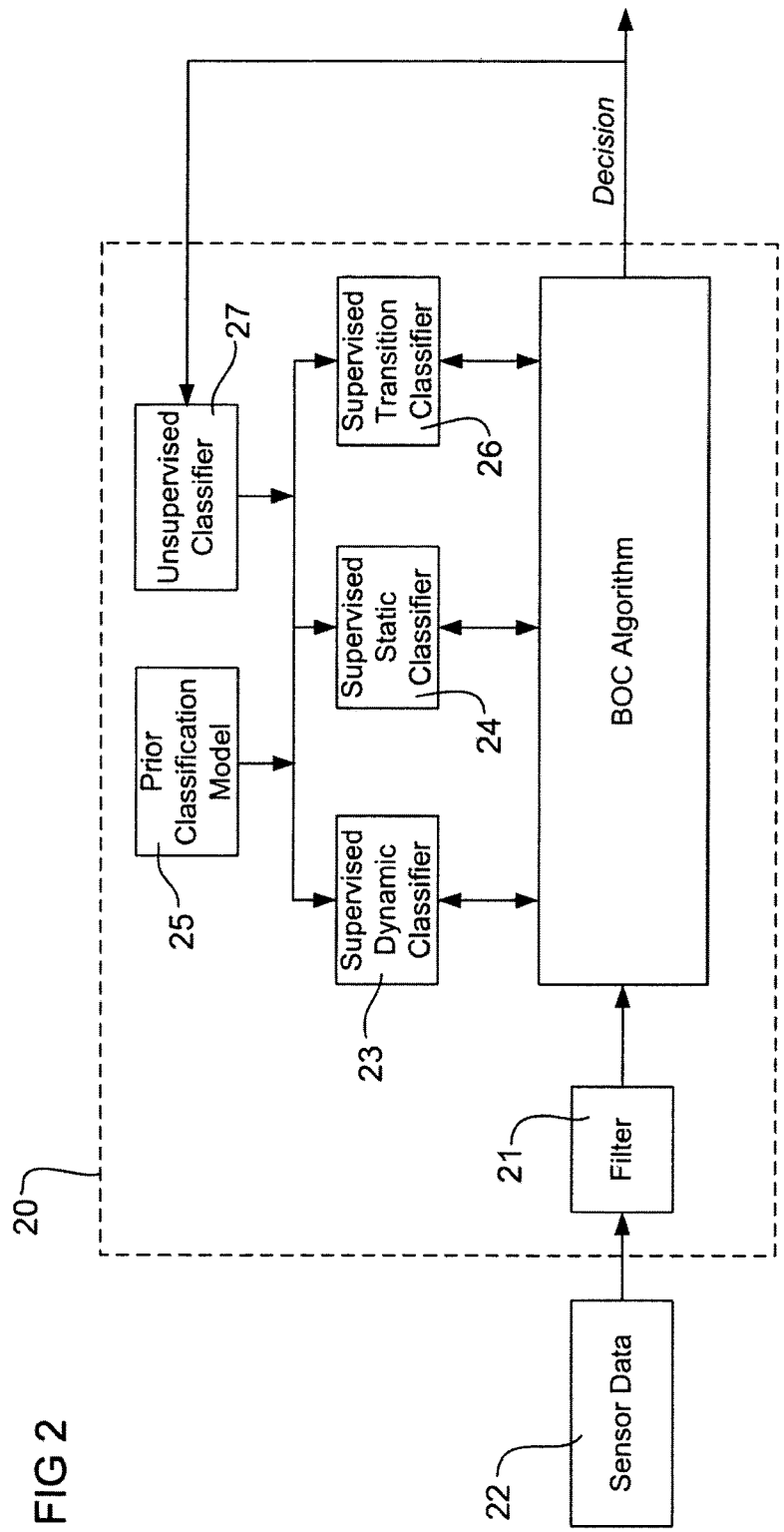
FIG. 2 shows a basic structure of a BOC algorithm according to one embodiment of the present invention.
Figure 3:
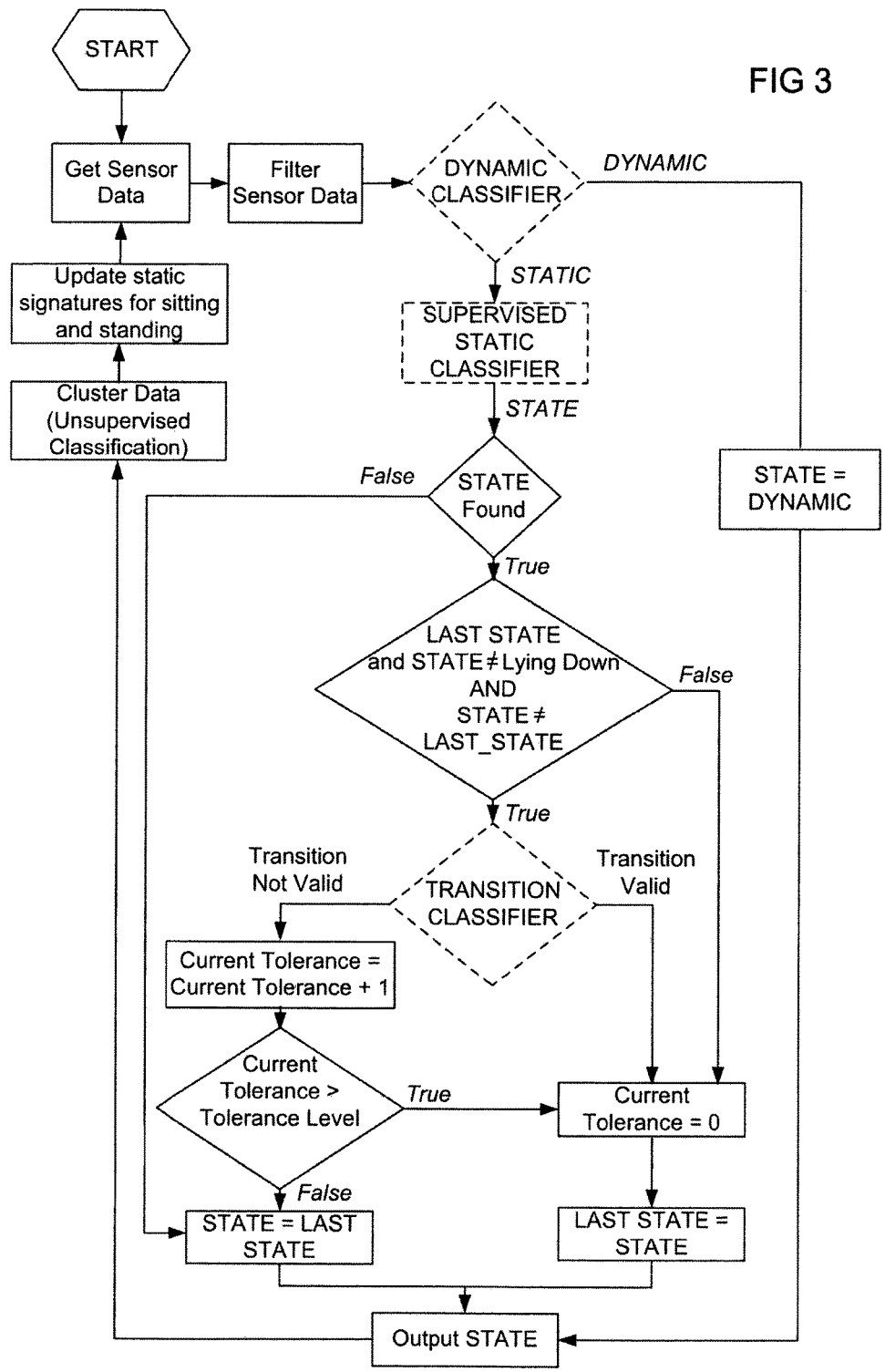
FIG. 3 shows a BOC algorithm flowchart.
Figure 4:
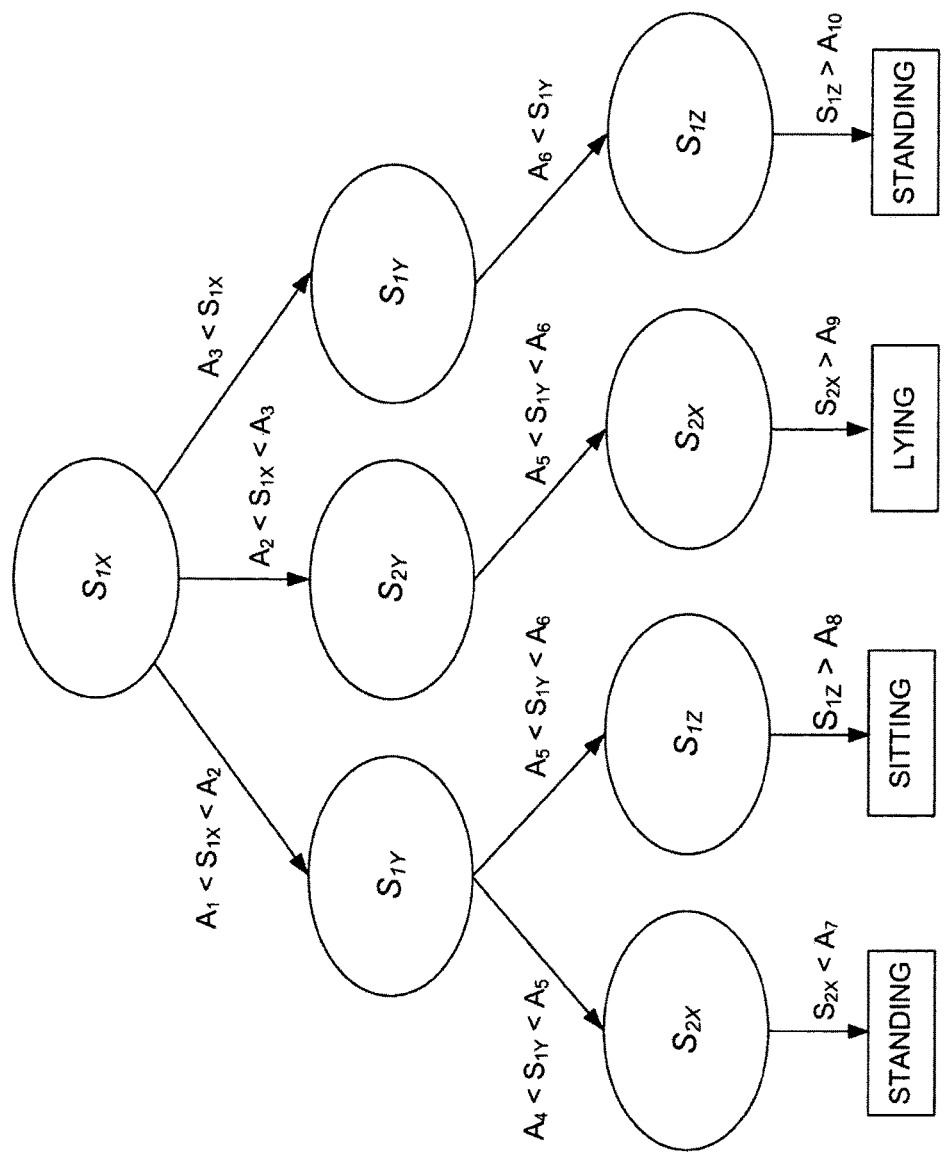
FIG. 4 shows an example logic tree.

Referring to FIGS. 2 to 4, BOC algorithm 20 may assign class signatures to primary body orientations including standing, sitting and lying down. Raw position sensor values show clear patterns when a person wearing a classification device is in one of these states. These patterns take the form of a sequence of discrete time-series G values, local earth field components and angular displacements in sagittal, coronal and transverse planes. An offline study with multiple subjects may be carried out to establish a set of patterns that hold true for a large population. Based on an established set of patterns and raw position sensor data for a given subject, the BOC algorithm may perform a classification as follows:

Step 1: Filtering of Data

Position sensors attached to human body are vulnerable to a number of environmental factors such as sudden movements, vibrations and occasional wireless dropouts. Since each such occurrence can produce inaccuracies in the task of identifying a pattern, the BOC algorithm 20 includes filter 21 to screen and to filter outliers from incoming position sensor data 22. Outliers in the sensor data 22 may take the form of sudden spikes in G readings or local earth field quantities and/or missing values. A number of techniques for smoothing data and interpolation to remove such errors are well known in the literature.

Step 2: Identification of Dynamic Movements

Similar to occasional perturbations due to environmental factors, dynamic human movements often produce large amplitude changes in position sensor data. Although such movements do not affect magnetometer readings it is desirable to detect significant changes in the inertial sensor to avoid misclassification. The BOC algorithm 20 includes supervised dynamic classifier 23 to allow it to identify dynamic movements. These may include activities such as jogging, running, walking, climbing stairs etc. Dynamic classifier 23 may exploit a characteristic that G values reported by inertial sensors exhibit a relatively smooth pattern when a person is either stationary or performs a flexion/extension or rotation movement while being at rest. On the other hand, dynamic movements such as running may lead to relatively high perturbations in inertial sensor data due to ground reaction forces acting on the human body during a movement. Typically, dynamic human movements follow a uniform pace. As a result perturbations in G values reported by inertial sensor/s during a dynamic movement may follow a cyclic pattern. Dynamic classifier 23 may continuously analyze the incoming data and may classify a current movement as dynamic as soon as a cyclic pattern in G values is identified. During dynamic movements, a main task of classification of orientation may remain suspended.

Step 3: Pattern Identification for Static Classification

BOC algorithm 20 includes supervised static classifier 24 to identify a posture based on pre-determined raw position sensor values and/or angular displacement data.

BOC algorithm 20 may use a logic tree based approach for pattern identification. FIG. 4 shows one embodiment of a logic tree approach based on inertial data alone. In FIG. 4, the notation Sik is used to refer to the G value along k axis for sensor i, while $A_j$, $j \in \{1, 2 \ldots 10\}$ represent a set of constants whose values are established in an offline training phase.

Prior classification model 25 sets out basic classification rules using a logic tree model during the training phase. Static classifier 24 may use the prior model 25 to map incoming position sensor values and angular displacements to the principal body orientations of sitting, standing and lying down.

Step 4: Iterative Validation

To provide a further test of accuracy of static classifier 24, BOC algorithm 20 includes supervised transition classifier 26. Transition classifier 26 may be used each time that static classifier 24 changes state. Transition classifier 26 may analyze recent position values to ascertain whether these values follow a clear pattern of transition from one state to the other. Humans often show common patterns of movement while transitioning from one body position to another. BOC algorithm 20 may exploit this characteristic to improve accuracy of classification of static body orientation.

Transition classification may be based on a hypothesis that a body posture "A" may be characterized not only by raw position values but also by a series of body movements and corresponding spine curvature shapes that preceded a subject's arrival at posture "A". For instance, transition classifier 26 may be invoked when a body position is shifted from sitting to standing or vice-versa. During an offline training phase, transition behavior from a typical sitting to standing (or vice-versa) orientation may be observed and defined using statistics on position values. Transition classifier 26 may compute and maintain some statistics on a moving window of position values in real time and may confirm whether a transition has in fact occurred. Based on this decision, BOC algorithm 20 may either pick the new state as returned by static classifier 24 or it may continue to use a last known state.

Step 5: Unsupervised classification based adaption of classifier rules

BOC algorithm 20 includes unsupervised classifier 27 to automatically adapt class signatures to individual subjects. Unsupervised classification (also known as data clustering) aims to classify data in absence of prior knowledge about class signatures.

Figure 5:
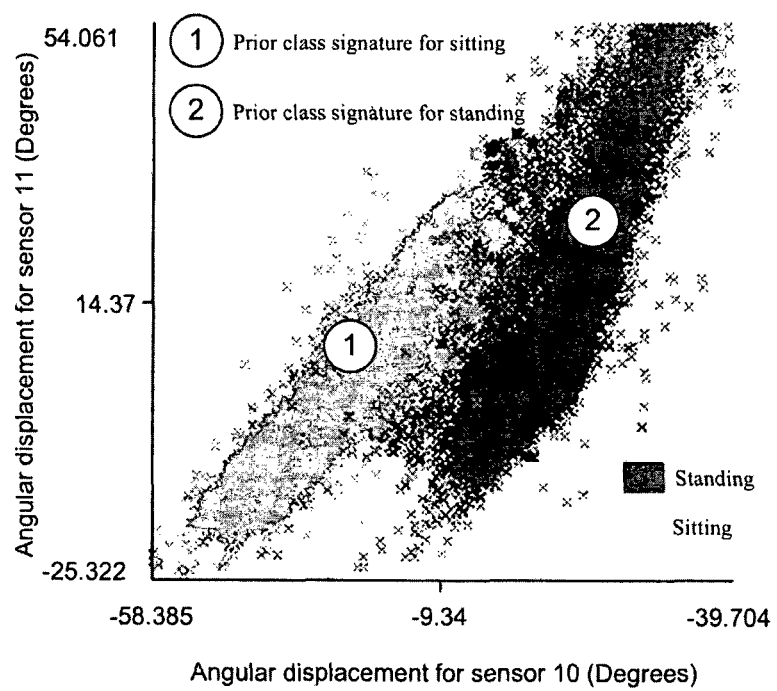
FIG. 5 shows an example to illustrate operation of an unsupervised classification module in the BOC algorithm.

FIG. 5 illustrates an example of an unsupervised classification process in a preferred embodiment of the present invention. The chart in FIG. 5 shows a scatter plot of the angular displacement data captured by two inertial sensors (10, 11) placed on the spine of a real subject. Points 1 and 2 on the scatter plot show the position of a prior signature, established during a training phase, for sitting and standing positions. In this example, the signatures are defined by a combination of angular data from the two sensors and hence can be plotted on the chart.

The unsupervised classification process is based on the assumption that during daily activities humans spend most time in a preferred sitting or standing position. For the example depicted in FIG. 5, this assumption can be validated by the presence of two clusters centered close to prior sitting and standing signature values. However, since the signatures are learned during a training process involving a large population and are not based on the current subject, the sitting and standing clusters are not exactly centered at signature values. According to the present invention, the unsupervised classification module may process incoming data and cluster it using a variant of a classical k-means clustering algorithm. The resulting clusters may then be matched against known a priori class signatures and signatures may be updated, if required. This process may ensure that BOC algorithm 20 adapts itself to individual subjects without requiring individualized calibration.

Finally, it is to be understood that various alterations, modifications and/or additions may be introduced into the constructions and arrangements of parts previously described without departing from the spirit or ambit of the invention.

The invention claimed is:

1. An apparatus for providing a classification of body orientation of a mammal in static and/or dynamic states, said apparatus including:
   two position sensors located on an upper body of the mammal to measure body position relative to a frame of reference and to provide first data indicative of said body position;
   a memory device coupled to the two position sensors and arranged for storing said first data at least temporarily;
   a processor to receive said first data and to process said first data to provide said classification of body orientation in said static and/or dynamic states, wherein said processor implements a Body Orientation Classification (BOC) algorithm for evaluating said body orientation, said BOC algorithm including:
      a dynamic classifier configured to identify dynamic movement based on identification of a cyclic pattern in the first data received from the two position sensors;
      a static classifier configured to identify posture based on the first data received from the two position sensors mapping to predetermined values; and
      a transition classifier configured to identify a pattern of transition in response to a changing state as identified by the static classifier and based on the first data received from the two position sensors comprising a moving window of position values in real time correlating to predefined statistics from observed data, wherein the correlation serves as a confirmation or refutation of the changing state; and
   wherein said BOC algorithm updates the predefined statistics based on said first data for subsequent classification of subsequent body position data in a feedback loop, and further outputs a status of the changing state.

2. The apparatus according to claim 1, wherein said two position sensors are located on a spine of the mammal.

3. The apparatus according to claim 1, wherein said processing is performed in real time to enhance accuracy of said classification.

4. The apparatus according to claim 1, wherein said algorithm is adapted to evaluate said body orientation based on assigning class signatures to primary body orientations including standing, sitting and lying down, and wherein said algorithm includes a logic tree to identify posture based on recognition of a signature or pattern relating to each posture.

5. The apparatus according to claim 4, wherein the signature or pattern relating to each posture is determined by a set of rules acquired during a training phase, and wherein the signature or pattern relating to each posture is modified by means of an unsupervised classifier.

6. The apparatus according to claim 5, wherein said unsupervised classifier clusters said first data and updates the signature or pattern based on distance to a center of a corresponding cluster in a d-dimensional space wherein d is the number of variables that defines the signature.

7. The apparatus according to claim 1, wherein said two position sensors include at least one of an accelerometer, a gyroscope and a magnetometer, and wherein said two position sensors are adapted to measure angular displacement along three orthogonal axes.

8. The apparatus according to claim 1, wherein said first data is used to derive one or more of:
   displacement in an extension flexion plane;
   displacement in a lateral flexion plane; and
   body rotation of said mammal.

9. The apparatus according to claim 1, wherein said two position sensors include at least one A to D converter for converting analog data to a digital domain, and wherein said A to D conversion takes place prior to storing said first data.

10. A method for providing a classification of body orientation of a mammal in static and/or dynamic states, said method including:
   measuring body position of the mammal relative to a frame of reference, said measuring being performed by two position sensors located on an upper body of the mammal to provide said classification of body orientation in said static and/or dynamic states;
   providing first data indicative of said body position from said two position sensors;
   storing said first data at least temporarily in a memory device;
   processing said first data by a processor to provide said classification of body orientation in said static and/or dynamic states by executing a Body Orientation Classification (BOC) algorithm for evaluating said body orientation, said BOC algorithm including:
      a dynamic classifier configured to identify dynamic movement based on identification of a cyclic pattern in the first data received from the two position sensors;
      a static classifier configured to identify posture based on the first data received from the two position sensors mapping to predetermined values; and
      a transition classifier configured to identify a pattern of transition in response to a changing state as identified by the static classifier and based on the first data received from the two position sensors comprising a moving window of position values in real time correlating to predefined statistics from observed data, wherein the correlation serves as a confirmation or refutation of the changing state;
   updating, by the processor, the predefined statistics based on said first data for subsequent classification of subsequent body position data in a feedback loop; and
   outputting, by the processor, a status of the changing state.

11. The method according to claim 10, wherein said two position sensors are located on a spine of a mammal.

12. The method according to claim 10, wherein said processing is performed in real time to enhance accuracy of said classification.

13. The method according to claim 10, wherein said algorithm is adapted to evaluate said body orientation based on assigning class signatures to primary body orientations including standing, sitting and lying down, and wherein said algorithm includes a logic tree to identify posture based on recognition of a signature or pattern relating to each posture.

14. The method according to claim 13, wherein the signature or pattern relating to each posture is determined by a set of rules acquired during a training phase, and including modifying the signature or pattern relating to each posture by means of an unsupervised classifier.

15. The method according to claim 14, wherein said unsupervised classifier clusters said first data and updates the signature or pattern based on distance to a center of a corresponding cluster in a d-dimensional space wherein d is the number of variables that defines the signature.

16. The method according to claim 10, wherein said two position sensors include at least one of an accelerometer, a gyroscope and a magnetometer, and wherein said two position sensors are adapted to measure angular displacement along three orthogonal axes.

17. The method according to claim 10, wherein said first data is used to derive one or more of:
   displacement in a lateral flexion plane;
   displacement in an extension flexion plane; and
   body rotation of said mammal.

18. The method according to claim 10, wherein each step of measuring includes converting analog data to a digital domain, and wherein the converting of data to the digital domain takes place prior to storing said first data.

* * * * *